United States Patent
Fanto et al.

(10) Patent No.: US 6,849,663 B2
(45) Date of Patent: Feb. 1, 2005

(54) 2-AMINOTETRALINES, A PROCESS FOR THEIR PREPARATION, AND PHARMACEUTICAL COMPOSITIONS, FOR THE PREVENTION AND THERAPEUTIC TREATMENT OF INFLAMMATORY AND/OR AUTOIMMUNE PATHOLOGIES

(75) Inventors: Nicola Fanto, Rome (IT); Gian Piero Moretti, Rome (IT); Piero Foresta, Pomezia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 131 days.

(21) Appl. No.: 09/816,317

(22) Filed: Mar. 26, 2001

(65) Prior Publication Data

US 2003/0158266 A1 Aug. 21, 2003

Related U.S. Application Data

(62) Division of application No. 09/533,381, filed on Mar. 22, 2000, which is a continuation of application No. PCT/IT98/00252, filed on Sep. 22, 1998.

(30) Foreign Application Priority Data

Sep. 22, 1997 (IT) ...................................... RM97A0568

(51) Int. Cl.$^7$ .......................................... A61K 31/135
(52) U.S. Cl. ...................................... 514/657; 514/656
(58) Field of Search ................................ 514/657, 656, 514/653, 654

(56) References Cited

U.S. PATENT DOCUMENTS

| 3,919,316 | A |   | 11/1975 | Molloy |   |
|---|---|---|---|---|---|
| 5,591,777 | A | * | 1/1997 | Foresta et al. | 514/653 |
| 5,962,525 | A | * | 10/1999 | Foresta et al. | 514/548 |
| 6,225,501 | B1 | * | 5/2001 | Moretti et al. | 564/413 |
| 6,242,497 | B1 | * | 6/2001 | Foresta et al. | 514/657 |

FOREIGN PATENT DOCUMENTS

| DE | 27 52 659 | 6/1978 |
|---|---|---|
| EP | 0 109 815 | 5/1984 |
| EP | 0 209 275 | 1/1987 |
| EP | 0 466 662 | 1/1992 |
| EP | 0 493 346 | 7/1996 |
| EP | 0 0730 861 | 9/1996 |
| WO | 98 33762 | 8/1998 |

OTHER PUBLICATIONS

Weinstock et al, "Synthesis and Dopaminergic Activity of Some Halogenated Mono– and Dihydroxylated 2–Amimotetralins", J. Medicinal Chemistry, 1986, vol. 29, No. 9, pp. 1615–1627.

Weinsock et al. "Synthesis and Dopaminergic Activity of Some Halogenated Mono– and Dihydroxylated 2–Aminotetralins" J. of Med. Chem. vol. 29, No. 9, Sep. 1986 pp 1615–1627.

Chemical Abstracts, vol. 97, No. 7, Aug. 1982 abstract No. 49225u, Horn et al Brain levels and metabolism of the dopaminenergic agonist 2–amino–6,7–dihydroxytetrahydronaphthalene after administration of various prodrugs: p. 12, col. 1 & J. Med. Chem. vol. 25, No. 18, 1982, pp 993–996.

Chemical Abstracts, vol. 96, No. 7, Feb. 1982, Abstract No. 46115b Horn et al Synthesis and activity of a metabolite of the dopaminenergic agonist 6,7–ADTN p. 237 col. 1 & Eur. J. of Med. Chem, Chimica Therapeutica vol. 16, No. 5, 1981 pp 469,472.

Chemical Abstracts vol. 75, No. 17, Oct. 1971 abstract No. 110101q, Violland Potential psaychotropic compounds p. 416 col. 2 & Chim. Ther., vol. 6, No. 3, 1971, pp 196–202.

Chemical Abstracts vol. 103, No. 15, Oct. 1985 abstract No. 123125x Nordlander A short enantiospecific synthesis of 2–amino–6,7–dihydroxy–1,2,3,4– tetrahydrona phthalene p. 693; col. 1; & J Org. Chem. vol. 50 No. 19, 1985 3619–3622.

* cited by examiner

Primary Examiner—Samuel Barts
(74) Attorney, Agent, or Firm—Nixon & Vanderhye P.C.

(57) ABSTRACT

2-Aminotetralines, a process for their preparation, and pharmaceutical compositions, for the prevention and therapeutic treatment of inflammatory pathologies (particularly septic shock) and/or autoimmune pathologies in which the aetiopathogenic role of inflammatory cytokines has been ascertained.

4 Claims, No Drawings

2-AMINOTETRALINES, A PROCESS FOR THEIR PREPARATION, AND PHARMACEUTICAL COMPOSITIONS, FOR THE PREVENTION AND THERAPEUTIC TREATMENT OF INFLAMMATORY AND/OR AUTOIMMUNE PATHOLOGIES

This application is a division of application Ser. No. 09/533,381, filed Mar. 22, 2000, which in turn is a continuation of PCT/IT98/00252 filed Sep. 22, 1998.

The invention described herein relates to derivatives of 2-aminotetralines and their pharmacologically acceptable salts, a process for their preparation, pharmaceutical compositions suitable for prophylactic and therapeutic treatment of septic shock, and for the treatment of inflammatory and/or autoimmune pathologies which will be better defined here below, in which the aetiopathogenetic role of inflammatory cytokines is well established.

6,7-Substituted-2-aminotetralines which are active in the treatment of septic shock are well known.

EP-A-0 730 861, which is incorporated herein for reference purposes, describes a class of such 6,7-substituted-2-aminotetralines and particularly the compound (R,S)-2-amino-6-fluoro-7-methoxytetraline (hereinafter referred to as ST 626).

The inflammatory and/or autoimmune pathologies to be treated with the compositions according to the invention described herein are, for example, rheumatoid arthritis, pancreatitis, inflammatory bowel disease, systemic lupus erythematosus, glomerulonephritis and encephalomyelitis.

Hereinafter, reference will be made only to septic shock, it being understood that the other pathologies due to inflammatory cytokines can also be effectively treated according to the invention.

Septic shock is an extremely severe clinical syndrome which may set in as a result of infections mainly caused either by gram-negative or gram-positive bacteria, by protozoa or by viruses, and characterised by leukocytosis, fever, tachycardia, hypotension and renal, respiratory, cardiac and hepatic insufficiency.

It should be stressed, however, that the severity of septic shock is independent of the type of micro-organism responsible for the syndrome (Parrillo J. E., Pathogenetic mechanisms of septic shock. *New Engl. J. Med.*, 328:1471–1477, 1993) but is related to the extent of the individual inflammatory response to the antigen responsible for the toxic insult.

Despite the significant improvement in antibiotic therapy and in intervention protocols in intensive care units, over the past few years, shock remains one of the major causes of morbidity and mortality in hospitalised patients. It is estimated that in the USA it is responsible for approximately 100,000 deaths/year (Glauser M. P., Zanetti G., Baumngartner J. D., Cohen J., Septic shock: pathogenesis. *Lancet*, 338:732–736, 1991).

The most decisive and characteristic feature of septic shock is the body's reaction to products deriving from lysis or from microbial metabolism.

The first of these substances to be identified and the one most used in experimental research is lipopolysaccharide (LPS); a constituent of the gram-negative bacteria wall, chemically consisting in a polysaccharide portion which varies according to the bacterial species, and a lipid portion (lipid A) which is constant, and present in the blood of septicaemic subjects in the form of micelles. If administered to animals, LPS is capable of reproducing all the cardiocirculatory and neurological symptoms encountered in shock (Olson. N. C., Salzer W. L., McCall C. E., Biochemical, physiological and clinical aspects of endotoxaemia. *Molec. Aspects Med.*, 10: 511–629, 1988). It is therefore identifiable as the prime mover in the chain of events which leads to the triggering of the clinical symptoms via activation of the intrinsic and extrinsic pathways of the coagulative cascade and the secretion of cytokines of mainly macrophage-monocyte origin, such as, for instance TNF, IL-1 and INF-γ (Bone R. C., A critical evaluation of new agents for the treatment of sepsis. *J. Am. Med. Ass.*, 266: 1686–1691, 1991).

The increasing importance this syndrome has come to take on over the past few years, its severity and the inadequate therapeutic means currently available make the rapid discovery of therapeutic agents capable of effectively combating the progression of the disease a highly desirable goal.

It has now been found that a new class of 6,7-substituted 2-aminotetralines exhibits potent activity in the prevention and therapeutic treatment of the above-mentioned pathologies.

2-Aminotetraline derivatives according to the invention can occur both as free bases with general formula (I):

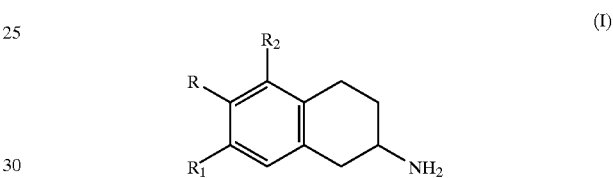

and as pharmacologically acceptable salts with general formula (II):

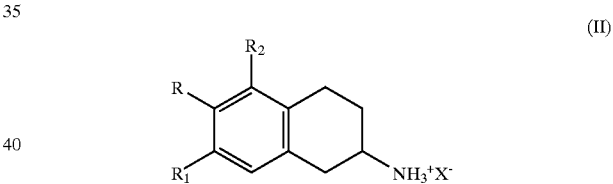

wherein:

R and $R_1$, are independently, halogen, particularly fluorine; hydroxy; C1–C4 alkoxy, particularly methoxy, optionally substituted in position ω with groups OH, $NH_2$, $NR_3R_4$, where $R_3$ and $R_4$ are independently H, C1–C4 alkyl, unsubstituted or substituted in position ω with groups OH, $NH_2$;

C1–C4 alkanoyl, particularly acetyl;

C1–C4 alkyl; carbamoyl; carbamoyloxy; amino; amino substituted $NR_3R_4$, where $R_3$ and $R_4$ have the above-mentioned meanings;

$R_2$ is hydrogen; halogen, particularly fluorine; hydroxy; methoxy, with the proviso that the case is excluded in which the 2-aminotetraline is a raceme in which (a) R=$R_1$=$CH_3O$; OH; $R_2$=H; or (b) R=F; $R_1$=$CH_3O$; OH; $R_2$=H; and $X^-$ is the monovalent anion of a pharmacologically acceptable acid.

What is meant by pharmacological acceptable salts of compounds of formula (II) are any of its salts with an acid that does not give rise to unwanted toxic or side effects. Such acids are well known to pharmacologists and to experts in pharmacy and pharmaceutical technology.

Examples of such salts—though not exclusively these—are chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate.

FDA approved salts are listed in *Int. J. of Pharm.* 33 (1986), 201–217, which is incorporated herein for reference purposes.

Preferred examples of specific compounds as per the invention described herein are:

S(−)-2-amino-6-fluoro-7-hydroxytetraline hydrochloride (ST 1237);

R(+)-2-amino-6-fluoro-7-hydroxytetraline hydrochloride (ST 1238);

(R,S)-2-amino-5,6-difluoro-7-methoxytetraline hydrochloride (ST 1269);

(R,S)-2-amino-6-fluoro-7-methyltetraline hydrochloride (ST 1275);

(R,S)-2-amino-7-fluoro-6-hydroxytetraline hydrochloride (ST 1267);

(R,S)-7-acetyl-2-amino-6-methyltetraline hydrochloride (ST 1274);

(R,S)-2-amino-7-fluoro-6-methoxytetraline hydrochloride (ST 1262).

The process for preparing the compounds according to the invention described herein either as free bases or as pharmacologically acceptable salts is reported in the following reaction schemes:

REACTION SCHEME 1

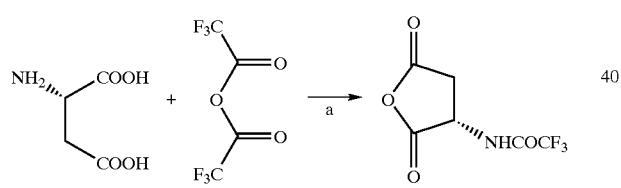

1

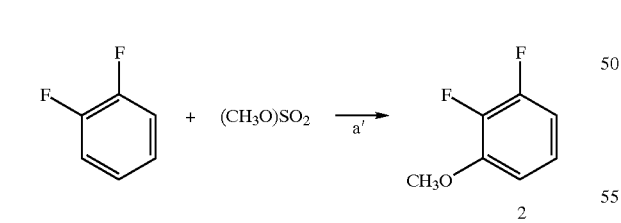

2

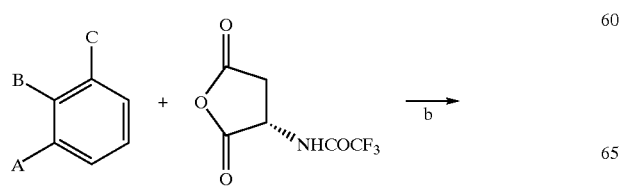

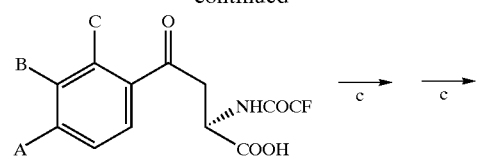

3

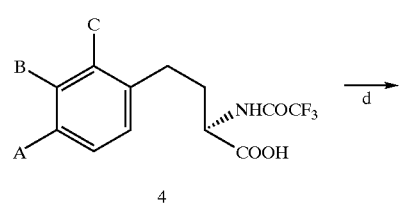

4

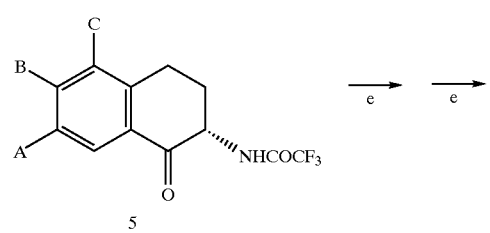

5

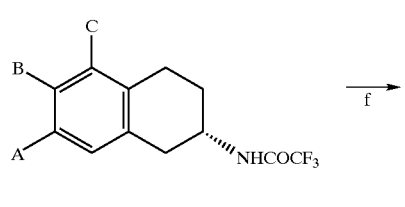

6

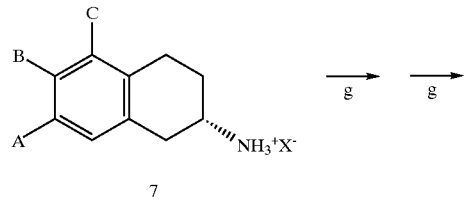

7

ST 1269 7c: A = OCH₃, B = F, C = F
ST 1275 7d: A = CH₃, B = F, C = H

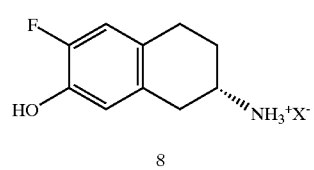

8

ST 1237 8a: S(−)
ST 1238 8b: R(+)

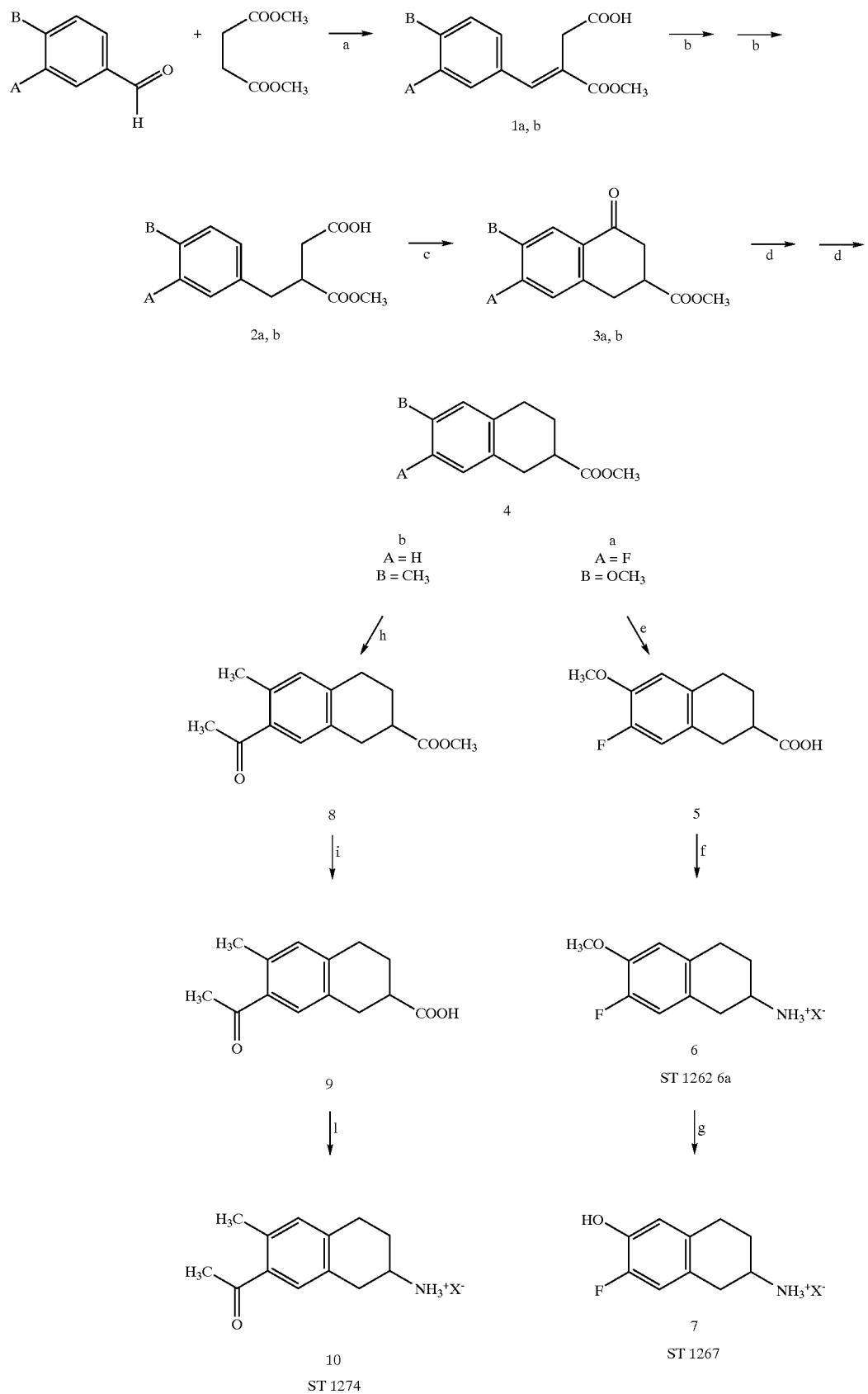

With reference to the above reaction schemes, the following examples, wherein X=Cl⁻, illustrate the invention without limiting it exclusively to these.

EXAMPLE 1

Scheme 1

Preparation of S(−)-2-amino-6-fluoro-7-hydroxytetraline hydro-chloride (ST 1237) 8a a) Preparation of S(−)-trifluoroacetyl-aspartic anhydride 1a L-Aspartic acid (100 g; 0.75 moles) was suspended in trifluoroacetic acid (300 mL), the resulting suspension was kept under stirring and cooled to −20° C. in an ice/salt bath. Trifluoroacetic anhydride (300 mL; 2.16 moles) was slowly added thereto under stirring. At the end of the addition the resulting mixture was cautiously refluxed at 45° C. overnight.

When the reaction ended, the solution was brought to dryness in an evaporator and the solid residue was washed three times with hexane under stirring, each time removing the hexane by decantation; the residue was again completely brought to dryness. Finally, the residue was triturated under stirring with hexane-ethyl ether, the resulting mixture was filtered and the residue was dried under vacuum. 150 g of compound 1a were obtained (yield 95%).

M.P.: 140–142° C.

$[\alpha]_D$=−40.7 (c=1% methyl alcohol)

$^1$H-NMR(DMSOd$_6$), Varian 300 MHz, δ(p.p.m.): 2.85–3.3 (2H,m,C$\underline{H}_2$); 4.95–5.1(1H,m,C$\underline{H}$NH); 9.6–9.8 (1H,bd,CHN$\underline{H}$COCF$_3$).

b) Preparation of S(+)-4-(3-fluoro-4-methoxyphenyl)-4-oxo-2-(N-trifluoro-acetyl)-aminobutanoic acid 3a S(−)-trifluoroacetyl-aspartic anhydride (150 g; 0.712 moles) was suspended in 2-fluoroanisole (300 mL; 2.67 moles), the resulting mixture was vigorously stirred and then anhydrous aluminium chloride (240 g; 1.57 moles) was slowly added in small portions. When the addition was completed, the mixture was kept under vigorous stirring at 40–45° C. for 24 h.

Anhydrous CH$_2$Cl and a further 60 g of AMCl$_3$ were added and the reaction mixture was kept under stirring for a further 48 h.

The solid residue was then treated with one liter of CH$_2$Cl$_2$ by grinding it under stirring. The methylene chloride containing the excess fluoroanisole was separated. The solid residue was filtered off and added portionwise to 2 liters of 6 M HCl kept under vigorous stirring. On completing the addition, the mixture was kept under stirring for 30 min. The acid phase was then repeatedly extracted with ethyl ether. The combined ether phases were washed with water, dried over anhydrous sodium sulphate and then brought to dryness. A raw solid residue was obtained which was crystallised by 1:1 AcOEt/hexane. 188 g of compound 3a were obtained (yield 78%).

M.P.: 113–115° C.

$[\alpha]_D$+27.5 (c=1% methyl alcohol)

$^1$H-NMR(CD$_3$OD), Varian 300 MHz, δ(p.p.m.): 3.6 (2H, m,C$\underline{H}_2$NH); 3.96(3H,S,PhOC$\underline{H}_3$); 4.88–5.01 (1H,m,CH$_2$C$\underline{H}$NH); 7.18–7.22 (1H,t,Ar); 7.7–7.8(1H,dd,Ar); 7.82–7.9 (1H,bd,Ar).

c) Preparation of S(+)-4-(3-fluoro-4-methoxyphenyl)-2-(N-trifluoroacetyl)-aminobutanoic acid 4a Compound 3a (100 g; 0.297 moles) was dissolved in trifluoro-acetic acid (500 mL). The resulting solution was cooled to 0° C. and triethylsilane (300 mL; 1.89 moles) slowly added. When the addition was complete, the mixture was slowly brought to its boiling point and kept at boiling temperature for 4 h.

The mixture was then brought to complete dryness in an evaporator; the residue was washed twice with ethyl ether, each time bringing the mixture to dryness to completely eliminate the trifluoracetic acid. The oily residue thus obtained was cooled to −20° C. in an ice/salt bath and then treated under stirring with an NaHCO$_3$ saturated solution whose pH had been adjusted to 10 with 4N NaOH.

The final alkaline phase was cautiously acidified to pH 3 with 6N HCl, at 0° C. A precipitate was obtained which was repeatedly extracted with CH$_2$Cl$_2$. The combined organic extracts were washed in a small amount of water, dried over anhydrous Na$_2$SO$_4$ and brought to dryness. The oily residue was dissolved in a small amount of ethyl acetate and precipitated with hexane under stirring. The mixture was kept under stirring overnight, filtered and the residue was dried. 72 g of compound 4a were obtained (yield 75%).

M.P.: 113–115° C.

$[\alpha]_D$=+11.3 (c=1% methyl alcohol) analysis: conforms to standards.

$^1$H-NMR(CDCl$_3$), Varian 300 MHz, δ(p.p.m.): 2.0–2.18 (1H,m,C$\underline{H}$HCHNH); 2.22–2.36 (1H,m,CH$\underline{H}$CHNH); 2.6–2.7(2H,t,PhC$\underline{H}_2$CH$_2$); 3.84(3H,S,PhOC$\underline{H}_3$); 4.6–4.7 (1H,m,CH$_2$C$\underline{H}$NH); 6.78(1H,bd,CHN$\underline{H}$COCF$_3$); 6.8–6.92 (2H,m,Ar).

d) Preparation of S(−)-2-(N-trifluoroacetyl)amino-6-fluoro-7-methoxy-1-tetralone 5a Compound 4a (70 g; 0.217 moles) was dissolved in anhydrous methylene chloride (1400 mL). The resulting mixture was cooled to 0° C. in an ice bath and then phosphorus pentachloride (70 g; 0.336 moles) was slowly added. At the end of the addition, the mixture was kept under stirring at 0° C. for about 2 h, and then cooled to −20° C. Aluminium chloride (56 g; 0.42 moles) was added to the mixture in small portions.

Following the addition, the mixture was kept for 2 h at room temperature and then cautiously heated to boiling point and kept at boiling temperature for about 6 h.

The mixture was then cooled to 0° C. and crushed ice (about 300 mL) was added portionwise under stirring to destroy the excess reactants. The mixture was extracted three times with CH$_2$Cl$_2$. The combined organic phases were dried over anhydrous Na$_2$SO$_4$ and brought to dryness. A yellowish solid was obtained which was dissolved in a small volume of ethyl acetate and then precipitated with hexane. 40 g of compound 5a were obtained (yield 60%).

M.P.: 184–185° C.

$[\alpha]_D$=−55.4 (c=1% methyl alcohol)

$^1$H-NMR (CDCl$_3$), Varian 300 MHz, (p.p.m.): 1.83–2.2 (1H,m,C$\underline{H}$HCHNH); 2.8–2.88 (1H,m,CH$\underline{H}$CHNH); 2.9–3.0 (1H,mC$\underline{H}$HCH$_2$); 3.15–2.26 (1H,m,CH$\underline{H}$CH2); 3.92(3H,S, PhOC$\underline{H}_3$); 4.53–4.62 (1H,m,CH$_2$C$\underline{H}$NHCOCF$_3$); 6.88 (1H, d,Ar.); 7.57 (1H,d,Ar.); 7.43 (1H,bs,CHN$\underline{H}$COCF$_3$).

e) Preparation of S(−)-2-(N-trifluoroacetyl)amino-6-fluoro-7-methoxy-tetraline 6a Compound 5a (40 g; 0.131 moles) was suspended in boroetherate trifluoride (340 mL) at 0° C. Triethylsilane (90 mL; 0.567 moles) was added to the suspension at 0° C., and the suspension was kept under stirring for 4 days at room temperature. At the end of the reaction a saturated solution of NaHCO$_3$ (pH 8–9) was added to the reaction mixture and the aqueous phase was extracted four times with CH$_2$Cl$_2$. The combined organic phases were washed with water, dried over anhydrous Na$_2$SO$_4$, filtered and brought to dryness.

The raw compound thus obtained was recrystallised from isopropyl ether. 30 g of compound 6a were obtained (yield 78%).

M.P.: 45–47° C.

$[\alpha]_D$=−80 (c=1% methyl alcohol)

$^1$H-NMR(CDCl$_3$), Varian 300 MHz, δ (.p.m.): 1.78–1.9 (1H,m,C$\underline{H}$HCNNH); 2.0–2.15 (1H,m,CH$\underline{H}$CHNH); 2.6–2.72 (1H,dd,PhC$\underline{H}$HCHNH); 2.73–2.9 (2H,m,PhCH$\underline{H}$ CHNH,PhC$\underline{H}$HCH2); 3.03–3.15 (1H,dd,PhCH$\underline{H}$CH$_2$) 4.2–4.35 (1H,m,C$\underline{H}$NH); 6.38 (1H,bd,CHN$\underline{H}$COCF$_3$); 6.6 (1H,d,Ar); 6.8 (1H,d,Ar).

f) Preparation of S(−)-2-amino-6-fluoro-7-methoxytetraline hydro-chloride 7a

Compound 6a (30 g; 0.13 moles) was dissolved in methanol (225 mL) and water (225 mL) containing $K_2CO_3$ (54 g; 0.391 moles).

The resulting solution was refluxed under stirring for 3 hours.

Methanol was removed under vacuum and a further 100 mL of water added to the solution.

The aqueous phase was repeatedly extracted with $CH_2Cl_2$. The combined organic phases were dried over anhydrous $Na_2SO_4$, filtered and brought to dryness. The oily solid thus obtained was dissolved in ethyl ether acidified with HCl (15% solution in ethanol) and the solid precipitate was filtered off and redissolved in methanol, decoloured with activated charcoal, filtered, concentrated under vacuum and finally crystallised with n-propanol.

Crystallisation was repeated twice giving 12.6 g of compound 7 (Yield 53%).

M.P.: 263–265° C.

$[\alpha]_D = -52.5$ (c=1% $H_2O$)

$^1$H-NMR (CDCl$_3$), Varian 300 MHz, δ ppm): 1.6–1.8 (1H, m,CHHCHN+); 2.0–2.15(1H,m,CHHCHN+); 2.6–2.75 (3H,m,PhCHHCHN+, PhCH$_2$CH$_2$); 2.95–3.05 (1H,DD,PhCHHCHN+); 3.45–3.55 1H, m, CHN+); 6.7–6.7 (2H,m,Ar).

g) Preparation of S(−)-2-amino-6-fluoro-7-hydroxytetraline hydro-chloride (ST 1237) 8a A solution of S(−)-2-amino-6-fluoro-7-methoxytetraline hydro-chloride 7a (3 g; 0.13 moles) in 20 mL of hydrobromic acid (47% aqueous solution) was kept at reflux temperature overnight. At the end of refluxing the solution was concentrated and brought to dryness under vacuum. The residue thus obtained was repeatedly washed under stirring with acetone and filtered off, redissolved in a 1:1 water/methanol mixture and eluted through a column containing 60 mL of Amberlyst A 21 resin, activated in basic form.

The eluate was acidified with 2 N hydrochloric acid and then concentrated to dryness under vacuum; the residue thus obtained was washed with acetone, filtered off and again dissolved in 1:1 water/methanol and eluted through a column containing 60 mL of Amberlyst A 21 resin activated in acid form.

The eluate was decoloured with activated charcoal, filtered through celite and concentrated in a small volume. Acetone was added thereto obtaining a precipitate that was filtered off and dried in the oven under vacuum.

2.2 g of compound 8a were obtained (yield 78%).

M.P.: 259–261° C.

$[\alpha]_D = -55.4$ (c=1% $H_2O$)

$^1$H-NMR (D$_2$O), Varian 300 MHz, δ (p.p.m.): 1.6–1.8 (1H, m, CH$_2$CHHCCHN$^+$); 2.0–2.1 (1H, m, CH$_2$CHH CHN$^{+}$ 2.5–2.7 (3H, m, PhCH$_2$CH$_2$), PhCHHN$^+$); 2.85–3.0 (1H, m, PhCHHN$^-$); 3.4–3.55 (1H, m, CHN+); 6.55–6.8 (2H, 2d, Ar.).

EXAMPLE 2

Scheme 1

Preparation of R(+)-2-amino-6-fluoro-7-hydroxytetraline hydro-chloride (ST 1238) 8b a) Preparation of R(+)-trifluoroacetyl Aspartic 1b The preparation is basically similar to that utilised for S(−)-trifluoro-acetyl-aspartic 1a using D(−)aspartic acid as the starting product (yield 86%).

M.P.: 142–144° C.

$[\alpha]_D = +40.0$ (c=1% methyl alcohol)

$^1$H-NMR: in accordance with and coinciding with that obtained with product 1a.

b) Preparation of R(−)-4-(3-fluoro-4-methoxyphenyl)-4-oxo-2-(N-trifluoroacetyl)aminobutanoic acid 3b The preparation is basically similar to that utilised for S(+)-4-(3-fluoro-4-methoxyphenyl)-4-oxo-2-(N-trifluoroacetyl)aminobutanoic acid 3a, using anhydride 1b as the starting material (yield 57%).

M.P.: 86–88° C.

$[\alpha]_D = -28.0$ (c=1% methyl alcohol)

$^1$H-NMR: in accordance and coinciding with that obtained with product 3a.

c) Preparation of R(−)-4-(3-fluoro-4-methoxyphenyl)-2-(N-trifluoroacetyl)aminobutanoic acid 4b The preparation is basically similar to that utilised for S(+)-4-(3-fluoro-4-methoxyphenyl)-2-(N-trifluoroacetyl)-aminobutanoic acid 4a using acid 3b as the starting material yield 65%).

M.P.: 110–112° C.

$[\alpha]_D = -11.2$ (c=1% methyl alcohol)

$^1$H-NMR: in accordance and coinciding with that obtained with product 4a.

d) Preparation of R(+)-2-(N-trifluoroacetyl)amino-6-fluoro-7-methoxy-1-tetralone acid 5b The preparation is basically similar to that utilised for S(−)-2-(N-trifluoroacetyl)-amino-6-fluoro-7-methoxy-1-tetralone acid 5a using anhydride 4b as the starting material (yield 84%).

M.P.: 185–186° C.

$[\alpha]_D = +66.0$ (c=1% methyl alcohol)

$^1$H-NMR: in accordance and coinciding with that obtained with product 5a.

e) Preparation of R(+)-2-(N-trifluoroacetyl)-amino-6-fluoro-7-methoxytetraline acid 6b The preparation is basically similar to that utilised for S(−)-2-(N-trifluoroacetyl)-amino-6-fluoro-7-methoxytetraline acid 6a using tetralone 5b as the starting material (yield 47%).

M.P.: 145–147° C.

$[\alpha]_D = +92.0$ (c=1% methyl alcohol)

$^1$H-NMR: in accordance and coinciding with that obtained with product 6a.

f) Preparation of R(+)-2-amino-6-fluoro-7-methoxytetraline hydro-chloride 7b

The preparation is basically similar to that utilised for S(−)-2-amino-6-fluoro-7-methoxytetraline hydrochloride 7a using tetraline 6b as the starting material (yield 64%).

M.P.: 260–262° C.

$[\alpha]_D = +48.5$ (c=1% $H^2O$)

$^1$H-NMR: in accordance and coinciding with that obtained with product 7a.

g) Preparation of R(+)-2-amino-5-fluoro-7-hydroxytetraline hydro-chloride (ST 1238) 8b The preparation is basically similar to that utilised for S(−)-2-amino-5-fluoro-7-hydroxytetraline hydrochloride (ST 1237) 8a using tetraline hydrochloride 7b as the starting material (yield 78%).

M.P.: 260–262° C.

$[\alpha]_D = +55.0$ (c=1% $H_2O$)

$^1$H-NMR (D$_2$O), Varian 300 MHz, δ (p.p.m.): 1.6–1.8 (1H,m,CH$_2$CHHCHN+); 2.0–2.1 (1H,m,CH$_2$CHHCHN+); 2.5–2.7(3H,m,PhCH$_2$CH$_2$)PhCHHCHN+); 2.85–3.0(1H, m, PhCHHCHN); 3.4–3.55(1H,m,CHN$^+$); 6.55–6.8(2H,2d, Ar.).

EXAMPLE 3

Scheme 1

Preparation of (R,S)-2-amino-5,6-difluoro-7-methoxytetraline hydrochloride (ST 1269) 7c a) Preparation of (R,S)-trifluoroacetyl-aspartic Anhydride 1c The preparation is basically similar to that utilised for S(−)-trifluoroacetyl-aspartic anhydride 1a using D,L-aspartic acid as the starting product (yield 96%).

M.P.: 133–134° C.

1HNMR: in accordance and coinciding with that obtained with product 1a.

a') Preparation of 2.3-difluoroanisole 2

20 g (0.154 moles) of 2.3-difluorophenol were salified by shaking the product at room temperature in a solution of 6.24 g of NaOH in 60 mL of water to completely dissolve it.

To the solution cooled to about 10° C., 14.4 mL of dimethyl sulphate, were slowly added; the solution was then heated to reflux temperature and refluxed for 24 h.

The reaction mixture was brought to room temperature and extracted with methylene chloride; the organic phase was washed with water, N sulphuric acid and again with water until a neutral pH was obtained.

The solution was dehydrated with anhydrous sodium sulphate and the solvent removed under vacuum to give 21 g of compound a' as a reddish oil which was analysed by NMR and utilised as it was (yield 94% on the raw material).

$^1$H-NMR (D$_2$O) Varian 300 MHz δ (p.p.m.): 3.9 (3H,S, PhOC$\underline{H}_3$); 6.6–7.2 (3H, m, aromatics).

b) Preparation of (R,S)-4-(2.3-difluoro-4-methoxyphenyl)-4-oxo-2(N-trifluoroacetyl)aminobutanoic acid 3c The preparation is basically similar to that utilised for S(+)-4-(3-fluoro-4-methoxyphenyl)-4-oxo-2(N-trifluoroacetyl)aminobutanoic acid 3a using anhydride 1c and 2,3-difluoroanisole as the starting products and 2 and 72 h as the reaction time instead of 48 h (yield 23%).

$^1$H-NMR (D$_2$O) Varian 300 MHz δ (p.p.m.): 3.9 (3H,S, PhOC$\underline{H}_3$); 6.6–7.2 (3H, m, aromatics).

c) Preparation of (R,S-4-(2,3-difluoro-4-methoxyphenyl)-2-(N-trifluoroacetyl)aminobutanoic acid 4c The preparation is similar to that utilised for S(+)-4-(3-fluoro-4-methoxyphenyl)-2-(N-trifluoroacetyl)aminobutanoic acid 4a using acid 3c as the starting product (yield 76%).

$^1$H-NMR (CDCl$_3$), Varian 300 MHz, δ (p.p.m.): 2.0–2.2 (1H, m, C$\underline{H}$HCHN+) 2.2–2.4 (1H,m,CH$\underline{H}$CHCN); 2.6–2.8 (2H,t,PhC$\underline{H}_2$CH$_2$); 3.86 (3H,S,PhOC$\underline{H}_3$); 4.6–4.72 (1H,bq, C$\underline{H}_2$CHNH); 6.6–6.7 (1H,bt,Ar); 6.75–6.88 (2H,m,Ar,CH N$\underline{H}$COCF$_3$).

d) Preparation of (R,S)-2-(N-trifluoroacetyl)amino-5,6-difluoro-7-methoxy-1-tetralone 5c The preparation is basically similar to that utilised for S(−)-(N-trifluoroacetyl)amino-6-fluoro-7-methoxy-1-tetralone 5a using acid 4c as the starting product and 3 h at reflux after the addition of aluminium chloride instead of 6 h as the reaction time (yield 26%).

$^1$H-NMR (CDCl3), Varian 300 MHz, δ (p.p.m.): 1.85–2.0 (1H, m, C$\underline{H}$HCHN+) 2.84–3.07 (2H,m,CH$\underline{H}$NH, PhC$\underline{H}$H CH$_2$); 3.13–3.24 (1H,m,PhCH$\underline{H}$CH$_2$); 3.93 (1H,S,PhO C$\underline{H}_3$); 4.55–4.65 (1H,m, CH$_2$C$\underline{H}$NH); 7.38–7.42 (1H,dd, Ar); 7.43-(1H,bs,CHN$\underline{H}$COCF$_3$).

e) Preparation of (R,S)-2-(N-trifluoroacetyl)amino-5,6-difluoro-7-methoxytetraline 6c The preparation is basically similar to that utilised for S(−)-(N-trifluoroacetyl)amino-6-fluoro-7-methoxytetraline 6a (example 1) using tetralone 5c as the starting product and 7 days instead of 4 as the reaction time (yield 46%).

$^1$H-NMR (CDCl$_3$), Varian 300 MHz, δ (.p.m.): 1.75–1.9 (1H, m, C$\underline{H}$HCHN+) 2.04–2.16 (2H,m,CH$\underline{H}$CHNH); 2.6–2.9 (3H,m,PhC$\underline{H}_2$CHNH, PhC$\underline{H}$HCH$_2$); 3.05–3.15 (1H, dd,PhCH$\underline{H}$CH$_2$); 3.84 (3H,s,PhOC$\underline{H}_3$); 4.2–4.33 (1H,m,C$\underline{H}$ NHCOCF$_3$); 6.22 (1H,bs,CHN$\underline{H}$COCF$_3$); 6.9–6.94(1H,bd, Ar).

f) Preparation of (R,S)-2-amino-5,6-difluoro-7-methoxy-1-tetraline hydrochloride ST (1269) 7c The preparation is basically similar to that utilised for S(−)-2-amino-6-fluoro-7-methoxytetraline hydrochloride 7a using tetraline 6c as the starting product and isopropanol as the crystallisation solvent (yield 62%).

M.P.: decomposes at 210° C.

$^1$H-NMR (D$_2$O), Varian 300 MHz, δ (p.p.m.): 1.6–1.8 (1H, m, CH$_2$C$\underline{H}$HCHN+) 2.0–2.2 (1H,m,CH$_2$CH$\underline{H}$CHN+, 2.5–2.9 (3H,m,PhC$\underline{H}$HCHN+,PhC$\underline{H}_2$CH$_2$); 2.9–3.1 (1H,m, PhCHC$\underline{H}$N$^{+)}$; 3.4–3.6 (1H,m,C$\underline{H}$N$^+$); 6.5–6.6(1H,d,Ar).

EXAMPLE 4

Scheme 1

Preparation of (R,S)-2-amino-6-fluoro-7-methyltetraline hydro-chloride (ST 1275) 7d a) Preparation of (R,S)-trifluoroacetyl aspartic anhydride 1c (See example 3)

b) Preparation of (R,S)-4-(3-fluoro-4-metyl-Phenyl)-4-oxo-2-(N-tri-fluoroacetyl)aminobutanoic acid 3d The preparation is basically similar to that utilised for S(+)-4-(3-fluoro-4-methoxyphenyl)-4-oxo-2-(N-trifluoroacetyl)aminobutanoic acid 3a using fluorotoluene as the starting product and 72 h instead of 48 h as the reaction time (yield 36%).

$^1$H-NMR (CDCl$_3$) Varian 300 MHz, δ (p.p.m.): 2.15 (3H, d, PhC$\underline{H}_3$); 3.35–3.42 (1H,dd,C$\underline{H}$HCHNH); 3.5–3.6(1H,dd, CH$\underline{H}$CHNH); 4.68–4.76 (1H,m,CH$_2$C$\underline{H}$NH); 6.85–6.95 (1H,t,Ar); 7.55–7.65 (2H,m,Ar); 8.0–8.1(1H,bd,CHN$\underline{H}$ COCF$_3$).

c) Preparation of (R,S)-4-(3-fluoro-4-metyl-phenyl)-2-(N-trifluoroacetyl)aminobutanoic acid 4d The preparation is basically similar to that utilised for S(+)-4-(3-fluoro-4-methoxyphenyl)-2-(N-trifluoroacetyl) aminobutanoic acid 4a using acid 3d as the starting product (yield 52%).

$^1$H-NMR (CDCl$_3$) Varian 200 MHz, δ (p.p.m.): 2.15 (3H, d, PhC$\underline{H}_3$); 2.0–2.4 (2H,dd,C$\underline{H}_2$CHNH); 2.5–2.7(2H,t, PhCH$_2$CH$_2$); 4.5–4.7 (1H,bq,CH$_2$C$\underline{H}$NH); 6.6–6.7 (1H,m, Ar); 6.75–6.95 (2H,m,Ar); 7.35–7.5 (1H,bd,CHN$\underline{H}$COCF$_3$).

d) Preparation of (R,S)-2-(N-trifluoroacetyl)amino-6-fluoro-7-methyl-1-tetralone 5d The preparation is basically similar to that utilised for S(−)-2-(N-trifluoroacetyl)amino-6-fluoro-7-methoxy-1-tetralone 5a using acid 4d as the starting product and 1 h at reflux instead of 2 h at room temperature, and, after the addition of aluminium chloride, 6 h at reflux as the reaction time (yield 80%).

$^1$H-NMR (CDCl$_3$) Varian 300 MHz, δ (p.p.m.): 1.83–2.0 (1H, d, C$\underline{H}$HCHNH); 2.3-(3H,d,PhC$\underline{H}_3$); 2.8–2.9(1H,m, CH$\underline{H}$CHNH); 2.92–3.03 (1H,m,C$\underline{H}$HCH$_2$); 3.13–3.25(1H, m,CH$\underline{H}$CH$_2$); 4.53–4.62 (1H,m,CH$_2$C$\underline{H}$NHCOCF$_3$); 7.2 (1H,d,Ar); 7.6(1H,d,Ar); 7.45(1H,bs,CHN$\underline{H}$COCF$_3$).

e) Preparation of (R,S)-2-(N-trifluoroacetyl)amino-6-fluoro-7-methyl-tetraline 6d The preparation is analogous to that utilised for S(−)-2-(N-trifluoroacetyl)amino-6-fluoro-7-methoxytetraline 6a, using tetralone 5d as the starting product (yield 60%).

¹H-NMR (CDCl₃) Varian 300 MHz, δ (p.p.m.): 1.75–1.9 (1H, m, CHHCHNH); 2.0–2.15 (1H,m,CHHCHNH); 2.2 (3H,s,PhCH₃); 2.6–2.7 (1H,dd,PhCHHCHNH); 2.7–2.9 (2H,m,PhCHHCHNH,PhCHHCH2); 3.03–3.15(1H,dd, PhCHHCH2) 4.25–4.35 (1H,m,CHNH); 6.2 (1H,b,s,NH COCF₃); 6.7(1H,d,Ar); 6.9 (1H,d,Ar).

f) Preparation of (R,S)-2-amino-6-fluoro-7-methyltetraline hydro-chloride (ST 1275) 7d The preparation is basically similar to that utilised for S(−)-2-amino-6-fluoro-7-methoxytetraline hydrochloride 7a, using tetraline 6d as the starting product (yield 67%).

M.P.: decomposes at 230° C.

¹H-NMR (CD₃OD) Varian 300 MHz, δ (p.p.m.): 1.7–1.9 (1H, m, CH₂CHHCHN⁺); 2.15–2.25 (1H,m,CH₂CH HCHN⁺); 2.19(3H,S,PhCH₃); 2.7–2.9 (3H,m,PhCHNH⁺, PhCH₂CH₂); 3.05–3.6(1H,m,PhCHHCHN+); 3.45–3.6(1H, m, CHNH₃+); 6.75–6.8 (1H,d,Ar); 6.95–7.0 (1H,d,Ar).

EXAMPLE 5

Scheme 2

Preparation of (R,S)-2-amino-6-methoxy-7-fluorotetraline hydro-chloride (ST 1262) 6a a) Preparation of 4-(6-methoxy-7-fluorophenyl)-3-carbomethoxy-3-butanoic acid 1a 9.4 g (0.061 moles) of 3-fluoro-p-anisaldheyde and 10 g (0.068 moles) of dimethyl succinate were dissolved in 15 mL of anhydrous methanol. The solution thus obtained was added dropwise at room temperature to a previously prepared solution of sodium methoxide 1.66 g (0.073 moles). The reaction mixture was refluxed for 3 h in a nitrogen atmosphere, then cooled and concentrated at half volume under vacuum.

The solution thus obtained was acidified with 2N HCl, cooling it in an ice bath, and then diluted with water until precipitation of the product occurred. The precipitate was filtered off and dissolved in a saturated solution of sodium hydrogen carbonate. The aqueous solution was repeatedly shaken with ethyl ether and re-acidified with 2N HCl and cooled in an ice bath.

The product was repeatedly extracted from the aqueous solution, with anhydrous sodium sulphate, and the solvent removed under vacuum obtaining a solid product which was crystallised with an ethyl acetate/n-hexane mixture, brought to dryness to give 5.5 g of acid 1a (yield 33%).

M.P.: 141–144° C.

¹H-NMR (CDCl₃), Varian 300 MHz, δ (p.p.m.): 3.55 (2H,s,CH₂COOH); 3.83 (3H,s,COOCH₃); 3.9(3H,s,PhO CH₃); 6.95–7.2 (3H,m,Ar); 7.8 (1H,s,CH=C).

b) Preparation of (R,S)-4-(6-methoxy-7-fluorophenyl)-3-carbomethoxybutanoic acid 2a 2 g (0.0075 moles) of 4-(6-methoxy-7-fluorophenyl)-3-carbomethoxy-3-butanoic acid were dissolved in 80 mL of ethyl acetate and then hydrogenated in Parr apparatus with 200 mg of palladium on charcoal at 5.5 p.s.i. hydrogen pressure for 1.5 h. The solution was filtered through celite and the catalyst and solvent removed under vacuum to give 1.9 g of oil which spontaneously crystallise (yield 93%).

¹H-NMR (CDCl₃), Varian 200 MHz, δ (p.p.m.) 2.3–2.45 (1H,m,CHCOOCH₃); 2.5–2.75 (2H, m, CH₂COOH); 2.8–3.1 (2H,m,PhCH₂); 3.6 (3H,s,COOCH₃; 3.8 (3H,s, PhOCH₃); 6.75–6.9(3H,m,Ar)

c) Preparation of (R,S)-6-methoxy-7-fluoro-4-oxo-1,2,3,4-tetrahydro-2-naphthoic acid ethyl ester 3a 5.6 g (0.021 moles) of (R,S)-4-(6-methoxy-7-fluorophenyl)-3-carbomethoxy-butanoic acid 2a were dissolved in 100 mL of anhydrous methylene chloride; 5 g (0.024 moles) of phosphorus pentachloride were added, and the temperature was maintained at 0° C. for 45 min. The temperature was brought to −10° C. and 3.6 g (0.027 moles) of aluminium chloride were added to the solution; the temperature was left to rise to 20° C. in 40 min, and then the solution was heated to reflux temperature for 1 h.

The solvent was evaporated under vacuum; 100 mL of cold water were added to the suspension which was extracted 3 times with 150 mL of ethyl acetate; the organic solution was dehydrated over anhydrous sodium sulphate and the solvent removed under vacuum to give 4.3 g of solid product (yield 81%).

¹H-NMR (CDCl₃), Varian 200 MHz, δ (p.p.m.) 2.3–2.45 (1H,m,CHCOOCH₃); 2.5–2.75 (2H, m, CH₂COOH); 2.8–3.1 (2H,m,PhCH₂); 3.6 (3H,s,COOCH₃; 3.8 (3H,s, PhOCH₃); 6.75–6.9(3H,m,Ar)

d) Preparation of (R,S)-6-methoxy-7-fluoro-1,2,3,4-tetrahydro-2-napthoic acid methyl ester 4a 6 g (0.024 moles) of the (R,S)-6-methoxy-7-fluoro-4-oxo-1,2,3,4-tetrahydro-2-naphthoic acid methyl ester 3a were dissolved in 100 mL of a mixture composed of anhydrous methanol and 50 mL of glacial acetic acid; the solution was placed in a Parr apparatus with 800 mg of palladium over charcoal at 50 p.s.i. hydrogen pressure for 4 h.

The catalyst was filtered off through celite and the solvent removed under vacuum, obtaining 5.5 g of solid product (yield 98%).

¹H-NMR (CDCl₃), Varian 300 MHz, δ (p.p.m.): 1.75–1.9 (1H,m,CHHCHCOOCH₃); 2.1–2.22(1H,m,CHHCHCOO CH₃); 2.6–2.8 (3H,m,PhCH₂CHCOOCH₃, CHCOOCH₃); 2.9 (2H,d,PhCH₂CH₂); 3.7 (3H,s,COOCH₃); 3.83 (3H,s, PhOCH₃); 6.62 (1H,d,Ar); 6.78 (1H,d,Ar).

e) Preparation of (R,S)-6-methoxy-7-fluoro-1,2,3,4-tetrahydro-2-naphthoic acid 5a 5.2 g (0.022 moles) of (R,S)-6-methoxy-7-fluoro-1,2,3,4-tetrahydro-2-naphthoic acid 4a were suspended in a solution composed of 2.2 g of potassium carbonate in 50 mL of 50% aqueous solution of methanol; the resulting solution was refluxed for 1 h.

The methanol was removed under vacuum and the solution diluted with 150 mL of water and washed with ethyl ether; the aqueous solution was acidified with 12 N HCl.

The precipitate thus obtained was filtered off and dried to give 4.8 g of product (yield 97%).

¹H-NMR (CDCl₃), Varian 300 MHz, δ (p.p.m.): 1.8–1.95 (1H,m,CHHCHCOOCH₃); 2.1–2.25 (1H,m,CHHCHCOO CH₃); 2.65–2.85(3H,m,PhCH₂CHCOOCH₃, CHCOOCH₃); 2.95(2H,d,PhCH₂CH₂); 3.82 (3H,s,PhOCH₃); 6.6(1H,d,Ar); 6.8(1H,d,Ar).

f) Preparation of (R,S)-2-amino-6-methoxy-7-fluorotetraline hydro-chloride (ST 1262) 6a 4.11 g (0.018 moles) of (R,S)-6-methoxy-7-fluoro-1,2,3, 4-tetrahydro-2-naphthoic acid 5a were dissolved in 9 mL of thionyl chloride under a nitrogen atmosphere and the solution was heated to 60° C. for 4 h; toluene was then added and the solution repeatedly extracted under vacuum.

A green oil was obtained which was dissolved in 12 mL of anhydrous acetone and added dropwise to a solution of sodium azide 1.75 g (0.024 moles) in 12 mL of water, cooling the reaction mixture to 0° C.

The mixture was left to react under stirring for 30 min leaving the temperature to rise to 20° C. The mixture was again cooled to 0–5° C. and 150 mL of water were added.

The precipitate thus obtained was brought to dryness under vacuum, obtaining 3.9 g of acid azide.

The product thus obtained was dissolved in 12 mL of toluene and heated for 30 min to 100° C.; the solvent was removed, obtaining a dense oil to which 10 mL of anhydrous benzyl alcohol were added, whereupon the solution was again heated at 100° C. for 6 h.

The solution was cooled to 5° C. overnight; the precipitate thus obtained was then filtered off and brought to dryness, obtaining 4.7 g of carbobenzoxy derivative.

The product was placed in 350 mL of anhydrous ethanol and dissolved by heating slightly, and acidified with about 2 mL of concentrated HCl; 500 mg of palladium over charcoal were added and the mixture thus obtained was placed in Parr apparatus and hydrogenated for 5 h at 50 p.s.i. hydrogen pressure.

The catalyst was filtered off over celite and repeatedly washed with heated ethanol; the solvent was removed under vacuum and the solid thus obtained was crystallised with an ethanol/ethyl ether mixture (yield 58%).

M.P.: decomposes at 230° C.

$^1$H-NMR (DMSOd$_6$), Varian 300 MHz, δ (p.p.m.): 1.6–1.8 (1H,m,C$\underline{H}$HCHN$^+$); 2.0–2.2 (1H,m,CH$\underline{H}$CHN$^+$); 2.6–3.0(4H,m,PhC$\underline{H}_2$CH$_2$CH$_2$,PhC$\underline{H}_2$CHNN+); 3.8 (3H,s, OC$\underline{H}_3$); 6.8–7.0(2H,2d,Ar)

EXAMPLE 6

Scheme 21 g) Preparation of (R,S)-2-amino-6-hydroxy-7-fluorotetraline hydro-chloride (ST 1267) 7

0.6 g (0.0026 moles) of (R,S)-2-amino-6-methoxy-7-fluorotetraline hydrochloride 6a were suspended in 8 mL of hydrobromic acid 47% solution in water and then heated to 130° C. overnight.

Water was removed by evaporation under vacuum; the dark solid thus obtained, dissolved in 50% aqueous solution of methanol, was eluted through a column of 20 mL of A-21 resin activated in a basic form.

The eluted solution was acidified to pH 2 with 3N hydrochloric acid, concentrated under vacuum and eluted through a column of 20 mL of A-21 resin activated in hydrochloride form.

The solvent was completely removed under vacuum.

The solid thus obtained was treated with acetone, filtered off and crystallised from methanol by addition of ethyl ether; 350 mg of product were obtained (yield 62%).

M.P.: decomposes at about 200° C.

$^1$H-NMR, (CD$_3$OD), Varian 300 MHz, δ (p.p.m.): 1.7–1.9 (1H,m,C$\underline{H}$HCHN+); 2.1–2.3 (1H,m,CH$\underline{H}$CHN+); 2.7–3.1 (4H,m,PhC$\underline{H}_2$CH$_2$; PhC$\underline{H}_2$CHN$^+$); 3.4–3.6 (1H,m,C$\underline{H}$N$^{30}$); 6.6–6.85(2H,2d,Ar).

EXAMPLE 7

Scheme 2

Preparation of (R,S)-2-amino-6-methyl-7-acetyltetraline hydro-chloride (ST 1274) 10 a) Preparation of 4-(6-methylphenyl)-3-carbomethoxy-3-butanoic acid 1b

The preparation is basically similar to that utilised for 4-(6-methoxy-7-fluorophenyl)-3-carbomethoxy-3-butanoic acid 1a, using p-tolualdehyde as the starting product, 3 h as the reaction time at reflux, and a cyclohexane/ethyl acetate mixture as the crystallisa-tion solvent yield 27%).

$^1$H-NMR(CDCl$_3$); Varian 200 MHz, δ (p.p.m.): 2.35 (3H, s,PhC$\underline{H}_3$); 3.58 (2H,s,C$\underline{H}_2$COOH); 3.83 (3H,s,COOC$\underline{H}_3$); 7.15–7.3 (4H,m, Ar); 7.87 (1H,s,C$\underline{H}$=C).

b) Preparation of 4-(6-methylphenyl)-3-carbomethoxy-3-butanoic acid 2b

The preparation is basically similar to that utilised for 4-(6-methoxy-7-fluorophenyl)-3-carbomethoxy-3-butanoic acid 2a, using acid 1b as the starting product, and 2.5 h as the hydrogenation time (yield 94%).

$^1$H-NMR (CDCl$_3$), Varian 200 MHz, δ (p.p.m.): 2.23 (1H,s,PhC$\underline{H}_3$); 2.28–2.45(1H,m,C$\underline{H}$COOCH$_3$); 2.55–2.75 (2H,m,C$\underline{H}_2$COOH); 2.9–3.1 (2H,m,PhC$\underline{H}_2$); 3.62 (3H,s, COOC$\underline{H}_3$); 6.9–7.1 (4H,m,Ar)

c) Preparation of (R,S)-6-methyl-4-oxo-1,2,3,4-tetrahydro-2-naph-thoic acid methyl ester 3b The preparation is basically similar to that utilised for (R,S)-6-methoxy-7-fluoro-4-oxo-1,2,3,4-tetrahydro-2-naphthoic acid methyl ester 3a, using acid 2b as the starting product (yield 94%).

$^1$H-NMR (CDCl$_3$), Varian 200 MHz, δ (p.p.m.): 2.35 (3H,s,PhC$\underline{H}_3$); 2.7–2.9(2H, m, PhC$\underline{H}_2$); 3.1–3.2 (3H,m, PhCOC$\underline{H}_2$,C$\underline{H}$COOCH$_3$); 3.7 (3H,s,COOC$\underline{H}_3$); 7.1–7.35 (2H,m,Ar); 7.8 (1H,s,Ar).

d) Preparation of (R,S)-6-methyl-1,2,3,4-tetrahydro-2-naphthoic acid methyl ester 4b The preparation is basically similar to that utilised for (R,S)-6-methoxy-7-fluoro-1,2,3,4-tetrahydro-2-naphthoic acid methyl ester 4a, using methyl ester 3b as the starting product (yield 94%).

$^1$H-NMR (CDCl$_3$), Varian 200 MHz, δ (p.p.m.): 1.7–1.95 (1H,m,C$\underline{H}$HCHCOCCl$_3$); 2.1–2.3 (1H,m, CH$\underline{H}$CHCOO CH$_3$); 2.3 (3H,s,PhC$\underline{H}_3$); 2.6–2.85 (3H,m,PhC$\underline{H}_2$CHCOO CH$_3$, C$\underline{H}$COOCH$_3$); 2.9–3.0 (2H,d,PhC$\underline{H}_2$CH$_2$); 3.72 (3H, s,COOC$\underline{H}_3$); 6.85–7.1 (3H,m,Ar)

h) Preparation of (R,S)-6-methyl-7-acetyl-1,2,3,4-tetrahydro-2-naphthoic acid methyl ester 8

3.8 g (0.0186 moles) of (R,S)-6-methyl-1,2,3,4-tetrahydro-2-naphthoic acid methyl ester 4b were dissolved in 30 mL of methylene chloride; 5.2 g of aluminium chloride were added to the solution cooled to 5° C. under a nitrogen atmosphere and 1.6 mL of acetyl chloride were added dropwise at the same temperature under stirring.

The reaction mixture was left to react at room temperature for 1.5 h, whereupon the mixture was cooled by adding 100 mL of cold water very slowly under stirring. The solution was repeatedly extracted with 100 mL (total volume) of methylene chloride and washed repeatedly with cold water.

The organic phase was anhydrified with anhydrous sodium sulphate, and the solvent removed under vacuum obtaining a dark solid, which was dried giving 3.8 g of raw product that was purified by silica gel column chromatography (50 mL), using n-hexane/ethyl acetate 8:2 as the solvent.

The solvent was removed under vacuum obtaining 1.8 g of product (yield 40%).

$^1$H-NMR (CDCl$_3$), Varian 300 MHz, δ (p.p.m.): 1.78–2.0 (1H,m,C$\underline{H}$HCHCOCOOCH$_3$); 2.1–2.3 (1H,m,CH$\underline{H}$CH COOCH$_3$); 2.45 (3H,s,COC$\underline{H}_3$); 2.55 (3H,s,PhC$\underline{H}_3$); 2.65–2.85 (3H,m,PhC$\underline{H}_2$CHCOOCH$_3$, C$\underline{H}$COOCH$_3$); 2.95 (2H, d,PhC$\underline{H}_2$CH$_2$); 6.95 (1H,s,Ar); 7.45 (1H,s,Ar).

i) Preparation of (R,S)-6-methyl-7-acetyl-1,2,3,4-tetrahydro-2-naphthoic acid 9

The preparation is basically similar to that utilised for (R,S)-6-methoxy-7-fluoro-1,2,3,4-tetrahydro-2-naphthoic acid 5, using methyl ester 8 as the starting product, 1.5 h at reflux temperature as the reaction time and n-hexane/ethyl acetate as the crystallisation mixture (yield 82%).

$^1$H-NMR (CDCl), Varian 300 MHz, δ (p.p.m.): 2.78–2.92 (1H,m,C$\underline{H}$HCHCOOH); 2.1–2.25(1H,m,CH$\underline{H}$CHCOOH); 2.4 (3H,s,COC$\underline{H}_3$); 2.5 (3H,s,PhC$\underline{H}_3$); 2.7–2.9 (3H,m,Ph C$\underline{H}_2$CHCOOH,C$\underline{H}$COOH); 2.9–3.0 (2H, d, PhC$\underline{H}_2$CH$_2$); 6.9 (1H,s,Ar); 7.4 (1H,s,Ar).

1) Preparation of (R,S)-2-amino-6-methyl-7-acetyltetraline hydrochloride (ST 1274) 10

6.5 g (0.028 moles) of (R,S)-6-methyl-7-acetyl-1,2,3,4-tetrahydro-2-naphthoic acid 9 were suspended in 40 mL of anhydrous acetone; 4.3 mL (0.0307 moles) of triethylamine were slowly added dropwise to the suspension. The solution temperature was brought to −5° C. and 2.95 mL (0.0307 moles) of ethyl-chlorophormiate dissolved in 4 mL of acetone were slowly added dropwise.

3.65 g (0.056 moles) of sodium azide dissolved in 80 mL of water were added dropwise to the solution maintaining the temperature at 0° C.; the mixture thus obtained was kept under stirring at 0° C. for 1 h, obtaining a precipitate. After the addition of a further 80 mL of cold water the solution was extracted with 100 is mL of toluene and the organic solution dehydrated with anhydrous sodium sulphate.

The solution was added to 30 mL of toluene heated to 100° C., and maintained at 100° C. for a further 1.5 hours.

The solvent was removed for evaporation under vacuum obtaining 4.9 g of dense lightly stained oil which was suspended in 50 mL of 8N HCl and heated to 100° C. under stirring for 1.5 h.

The solvent was removed for evaporation under vacuum; 100 mL of water were then added and the suspension was brought to pH 10 under stirring with 4 N sodium carbonate cooling in an ice bath.

The aqueous solution was divided into smaller amounts and extracted with 120 mL of ethyl ether. The organic phase was dehydrated with anhydrous sodium sulphate and gaseous hydrochloric acid was bubbled into the ether solution thus obtained.

The precipitate thereby obtained was filtered off under vacuum and dried in air to give 2.3 g of slightly stained solid that was crystallised with a mixture of ethyl acetate/methanol.

The solid was brought to dryness in the oven to give 2 g of colourless crystalline product (yield 30%).

M.P.: 195–197° C. with decomposition.

$^1$H-NMR, (CD$_3$OD), Varian 300 MHz, δ (p.p.m.): 1.75–1.85 (1H,m,C$\underline{H}$HCHN$^+$); 2.15–2.3 (1H,m,CH$\underline{H}$CHN+); 2.42 (3H,s,C$\underline{H}_3$CO); 2.53 (3H,s,C$\underline{H}_3$Ph); 2.8–3.0 (4H,m,PhC$\underline{H}_2$CHN+),PhC$\underline{H}_2$CH$_2$); 3.5–3.65 (1H,m, C$\underline{H}$N$^+$); 7.05 (1H,s,Ar); 7.6 (1H,s,Ar).

The methodological approach most widely employed for the purposes of assessing the possible protective effect of a substance in septic shock, in pre-clinical investigations, is the use of experimental models of intoxication with a toxic substance (exo- or endotoxin) injected directly into the laboratory animal or released in massive amounts by the infecting cells with which the animal is inoculated.

The description of the following pharmacological tests shows the results obtained with some of the compounds according to the invention, in comparison with the reference compound (R,S)-2-amino-6-fluoro-7-methoxytetraline hydrochloride (ST 626).

As mentioned above, the compound ST626 is an already known compound, which is structurally similar to the compounds of the invention and has a similar pharmacological activity.

These results demonstrate the preventive and therapeutical efficacy of the compounds of the invention, and also provide indications as to the possible mechanisms of action responsible for the favourable pharmacological profile of the compounds, namely a drastic lowering of inflammatory cytokine levels (TNF, IL-1β, IL-6 and IFN-γ) in the blood.

Evaluation of the Effect of ST 1238, ST 1274 and ST 1275 in Murine Models of Septic Shock Male BALB/C mice (C. River) aged approx. 6 weeks were utilised (10 animals per experimental group).

The animals, housed in cages at 22±2° C. and 50±15% relative humidity with 12 h of light (7 am–7 pm) and 12 h of darkness (7 pm–7 am) had unrestricted access to food and drinking water.

The substances utilised were: LPS (*Escherichia coli* serotype O26:B6), batch 73570 (Difco), LPS (*Salmonella typhosa*) batch 81H4018 (Sigma), SEB (*Staphylococcus aureus*), batch 144H4024 (Sigma), and D-galactosamine batch 031EE002485 (Merck).

The compounds tested were ST1238, ST 1274 and ST 1275.

The compound solution pH was corrected, where necessary, with NaOH 0.1 N (maintaining the solution cold and under stirring) to obtain values no lower than pH 5.5.

Lethality Induced by *S. typhosa* LPS

Animals were treated intraperitoneally (i.p.) with *S. typhosa* LPS. Prior to use, the endotoxin was first dissolved in sterile saline and then injected in a volume of 200 μL, at the dose of 27.0 mg/kg, corresponding to about the LD$_{80}$.

The compounds tested were administered intravenously (i.v.) in a volume of 200 μL of sterile saline at the dose approximately corresponding to ¹⁄₁₀ LD$_{50}$, 30 min before and again 5 min after the endotoxic challenge (LPS).

Lethality Induced by *E. coli* LPS in Mice Sensitised with D-Galactosamine

Animals were sensitised with D-galactosamine (1000 mg/kg, i.p.) and, at the same time, treated with *E. coli* LPS (0.30 mg/kg, i.p.) in a total volume of 200 μL.

The dose of LPS utilised corresponded approximately to ¹⁄₁₀ LD$_{50}$ in the animals sensitised with D-galactosamine.

The compounds tested were administered intravenously (i.v.) in a volume of 200 μL of sterile saline, at the dose approximately corresponding to ¹⁄₁₀ LD$_{50}$, 30 min before and 5 min after, or 5 and 30 min after the LPS challenge.

Lethality Induced by SEB (*Staphylococcus aureus*) in Mice Sensitised with D-Galactosamine Animals were sensitised with D-galactosamine (1000–1500 mg/kg, i.p.) and, at the same time, treated with the enterotoxin SEB (3 mg/kg, i.p.) in a total volume of 200 μL. The dose of SEB utilised corresponding to approximately the LD$_{80}$, was evaluated in a preliminary experiment.

The compounds tested were administered intravenously (i.v.) in a volume of 200 μL of sterile saline, at the dose approximately corresponding to ¹⁄₁₀ LD$_{50}$, 30 min before and 5 min after, or 5 min and 30 min after the SEB challenge.

Survival was assessed daily for 10 days in all the experiments, taking note of the day when each animal died.

The statistical significance of the protective effect was evaluated using a one-tailed Fisher's exact test.

Results

Lethality Induced by *S. typhosa* LPS

In this experimental model of endotoxic shock with *S. typhosa* LPS, the compounds ST 1274 and ST 1275 significantly reduce the lethality when administered pre- and post-challenge (p<0.01 and p<0.05, respectively) (Table 1).

TABLE 1

Effect of ST 1274 and ST 1275 i.v. administration on the
lethality induced in mice by injection of S. typhosa LPS.
Pre-/post-challenge treatment schedule (−30 and +5 min).

| Treatment (dose) | Dead/Total | Survival increase[a] (%) | P[b] |
|---|---|---|---|
| LPS control | 14/20 | — | — |
| ST 626 (6 mg/kg, i.v.) | 6/20 | +40 | <0.05 |
| LPS control | 18/20 | — | — |
| ST 1274 (5.5 mg/kg, i.v.) | 10/20 | +40 | <0.01 |
| LPS control | 10/10 | — | — |
| ST 1275 (4 mg/kg, i.v.) | 6/10 | +40 | <0.05 |

[a]= Percentage increase in survival of treated animals compared to LPS control.
[b]= Statistical significance evaluated by one-tailed Fisher's exact test.

Lethality Induced by *E. coli* LPS in Mice Sensitised with D-Galactosamine

Compound ST1238 significantly reduces the lethality with both temporal treatment protocols adopted (p<0.001 and p<0.01) (Tables 2 and 3), whereas compounds ST 1274 and ST 1275 give rise to non-significant percentage increases in survival (20%) only with the pre- and post-challenge administration protocol (Table 2).

TABLE 2

Effect of ST 1238, ST 1274 and ST 1275 i.v. administration
on the lethality induced by injection of *E. coli* LPS in mice
sensitised with D-galactosamine. Pre-/post-challenge
treatment schedule (−30 and +5 min).

| Treatment (dose) | Dead/Total | Survival increase[a] (%) | P[b] |
|---|---|---|---|
| LPS + D-GalN control | 25/29 | — | — |
| ST 626 (6 mg/kg, i.v.) | 21/28 | +11 | ns |
| LPS + D-GalN control | 17/20 | — | — |
| ST 1238 (18 mg/kg, i.v.) | 5/20 | +60 | <0.001 |
| LPS + D-GalN control | 7/10 | — | — |
| ST 1274 (5.5 mg/kg, i.v.) | 5/10 | +20 | ns |
| LPS + D-GalN control | 7/10 | — | — |
| ST 1275 (4 mg/kg, i.v.) | 5/10 | +20 | ns |

[a]= Percentage increase in survival of treated animals compared to control.
[b]= Statistical significance evaluated by one-tailed Fisher's exact test.

TABLE 3

Effect of ST 1238 i.v. administration on the lethality
induced by injection of *E. coli* LPS in mice sensitised with
D-galactosamine. Post-challenge only treatment schedule
(+5 and +30 min).

| Treatment (dose) | Dead/Total | Survival increase[a] (%) | P[b] |
|---|---|---|---|
| LPS + D-GalN control | 16/20 | — | — |
| ST 1238 (18 mg/kg, i.v.) | 7/19 | +44 | <0.01 |

[a]= Percentage increase in survival of treated animals compared to control.
[b]= Statistical significance evaluated by one-tailed Fisher's exact test.

Lethality Induced by SEB (*Staphylococcus aureus*) in Mice Sensitised with D-Galactosamine With this experimental model all the compounds reduce the lethality in comparison with controls (70%–90%) when administered 30 min before and 5 min after the challenge (Table 4). ST 1238 still maintains an extremely significant protective effect in the post-challenge only treatment schedule (p<0.001) (Table 5).

TABLE 4

Effect of ST 1238, ST1274 and ST 1275 i.v. administration
on the lethality induced by injection of LPS from SEB
enterotoxin in mice sensitised with D-galactosamine.
Pre- and post-challenge treatment schedule (−30 and +5 min).

| Treatment (dose) | Dead/Total | Survival increase[a] (%) | P[b] |
|---|---|---|---|
| SEB + D-GalN control | 15/20 | — | — |
| ST 1238 (18 mg/kg, i.v.) | 1/20 | +70 | <0.001 |
| SEB + D-GalN control | 9/10 | — | — |
| ST 1274 (5.5 mg/kg, i.v.) | 0/10 | +90 | <0.001 |
| SEB + D-GalN control | 9/10 | — | — |
| ST 1275 (4 mg/kg, i.v.) | 1/10 | +80 | <0.01 |

[a]= Percentage increase in survival of treated animals compared to control.
[b]= Statistical significance evaluated by one-tailed Fisher's exact test.

TABLE 5

Effect of ST 1238 i.v. administration on the lethality
induced by injection of LPS from SEB enterotoxin in mice
sensitised with D-galactosamine.
Post-challenge only treament schedule (+5 and +30 min).

| Treatment (dose) | Dead/Total | Survival increase[a] (%) | P[b] |
|---|---|---|---|
| SEB + D-GalN control | 18/20 | — | — |
| ST 1238 (18 mg/kg, i.v.) | 4/20 | +70 | <0.001 |

[a]= Percentage increase in survival of treated animals compared to LPS control.
[b]= Statistical significance evaluated by one-tailed Fisher's exact test.

Evaluation of the Effect of ST 1238 on Serum TNF (Tumor Necrosis Factor) Levels Induced by LPS in Rat Blood Culture Cultures of whole blood cells stimulated by LPS were utilised as an experimental model. This model, albeit with certain limitations, mimics the physiopathological aspects of endotoxiaemia, a syndrome in which gram-negative bacteria release lipopoly-saccharide into the blood-stream which thus comes into contact with the immune system cells.

In fact, this model has recently been adopted for the evaluation of potential inhibitors of the release of TNF and IL-1 (GC Rice et al., *Shock*, 4:254–266, 1994. A J H Gearing et al., *Nature*, 370:555–557, 1994. K Tschaikowsky, *Biochim. Biophys. Acta*, 1222:113–121, 1994. A Haziot et al, *J. Immunol.*, 152:5868–5876, 1994).

Male Wistar rats (C. River) weighing about 175–200 g were utilised.

The animals, housed in cages at 22±2° C. and 50±15% relative humidity with 12 h of light (7 am–7 pm), had unrestricted access to food and drinking water.

The compound tested was ST 1238.

The endotoxin utilised was: LPS from *Salmonella typhosa* batch 81H4018 (Sigma).

Treatment of Blood Samples

Heparinised blood samples, 0.450 mL/vials, were taken from Wistar rats sacrificed by decapitation.

Volumes of 0.025 mL (solution 20x) of the test compounds (final concentration of 0.050 mM) dissolved in sterile saline were added to the vials containing the blood samples.

0.025 mL (sol 20x) of *Salmonella typhosa* LPS (final concentration in LPS equal to 1 μg/mL) were added to the samples incubated for 1 h at 37° C. in a humidified atmosphere with 5% $CO_2$.

The samples were incubated in the same conditions for 4 h and then centrifuged for 5 min at 10,000 rpm and the supernatant was stored at −80° C. pending TNF assay.

TNF biological activity was determined in RPMI medium containing 1% FCS.

TNF Biological Assay

For the TNF assay serial dilutions of the samples (50 $\mu$L) containing TNF were made directly into Primaria 96-well microtiter plates; actinomycin D-mannitol (50 $\mu$L) at a final concentration of 4 $\mu$g/mL, prepared in RPMI medium added with 1% FCS, was added to the wells. This inhibitor enhances the cells sensitivity to TNF.

100 $\mu$L of a suspension (standardised at 4×10$^5$ cells/mL) of L929 (murine fibrosarcoma sensitive to the toxic action of TNF) were dispensed into each well. Appropriate controls, i.e. the actinomycin-D control (cells+actinomycin-D but without TNF) and the cell control (cells+culture medium alone) were also prepared.

After further incubation for 18 h at 37° C. with 5% $CO_2$, the cells were stained with a freshly prepared solution of 1 mg/mL XTT (sodium 3'-[1-[(phenylamino)-carbonyl]-3,4-tetrazolium]-bis(4-meth-oxy-6-nitro)benzene-sulphonic acid hydrate) and 125 $\mu$M PMS (phenazine methosulphate) according to the method described here below.

The XTT is dissolved (1 mg/mL) in RPMI medium at 60° C.

The PMS mother solution 100 mM (stable for about 20 days at +4° C. in the dark) is prepared by dissolving the PMS in PBS followed by brief sonication so as to fully dissolve the PMS. The 100 mM PMS solution is then diluted 1:800 in XTT, obtaining a final concentration of 125 $\mu$M in PMS and 1 mg/mL in XTT. The staining mixture must be filtered prior to use.

Cells were stained by adding 50 $\mu$L/well of the XTT-PMS staining solution, obtaining a final volume of 250 $\mu$L/well with final concentrations of 0.2 mg/mL in XTT and 25 $\mu$M in PMS, respectively. A "blank was also prepared in wells containing 200 $\mu$L of culture medium +50 $\mu$L of XT-PMS solution.

The microtiter plates are incubated for 2–2.5 h at 37° C. with 5% $CO_2$ (total incubation time=about 20 h).

The absorbance values of each sample were measured with a microtiter plate reader at a reading wavelength of 450 nm and a reference wavelength of 620 nm (the microtiter plate reader was programmed to deduct the value obtained for the "blank" from the sample value).

The TNF titre was calculated using the following method. By definition, 1 unit of biological activity is given by the semimaximal value (=50%) of the actinomycin-D absorbance.

Sample dilutions give rise to an absorbance value curve whose linear portion is described by the equation y=ax+b.

After inserting the a and b values (obtained from the linear regression analysis done by the computer) and after substituting the semimaximal absorbance value (corresponding to 1 biological unit) of the actinomycin-D control for y, the equation is solved for x, which represents the reciprocal of the sample dilutions.

The value obtained gives the TNF titre in U/mL.

Data were analysed statistically using the two-tailed Student's t test.

Results

The results obtained (Table 6) show that compound ST 1238 reduces (39%) TNF production by rat blood cultures stimulated with LPS.

TABLE 6

Effect of ST 1238 on TNF production induced in rat blood cultures (n = 5) stimulated with *S. typhosa* LPS (1 $\mu$g/mL). The compounds were tested at a concentration of 50 $\mu$M. The experimental conditions are those described in Materials and Methods.

| Treatment | TNF (mean % values) | Stand. Dev. | P* |
|---|---|---|---|
| LPS control | 100 | 0 | — |
| LPS + ST 1238 | 61 | 25 | <0.01 |

*Statistical significance evaluated by two-tailed Student's t test

Evaluation of the Effect of ST 1238 on Serum TNF Levels in Two Murine Shock Models Male BALB/c mice (C. River), aged approx. 6 weeks were utilised (10 animals per experimental group).

The animals, housed in cages at 22±2° C. and 50±15% relative humidity with 12 h of light (7 am–7 pm) and 12 h of darkness (7 pm–7 am), had unrestricted access to food and drinking water.

The compound tested was ST 1238.

The substances utilised were: LPS (from *E. coli* serotype O26:B6, batch 73570 JB (Difco), SEB (*Staphylococcus aureus*) batch 144H4024 (Sigma), D-galactosamine batch 031EE002485 (Merck).

Lethality Induced by *E. coli* LPS in Mice Sensitised with D-Galactosamine

The experimental conditions were exactly the same as those previously described.

Lethality Induced by SEB (*Staphylococcus aureus*) in Mice Sensitised with D-Galactosamine The experimental conditions were exactly the same as those previously described.

Blood Samples

In both experimental models, blood samples were taken 90 min after the challenge (peak serum TNF level).

Ether-anaesthetised mice were bled by retro-orbital sinus puncture.

Blood samples were incubated at room temperature for 2 h and the serum thus obtained was centrifuged for 20 min at 3000 rpm and stored at −80° C. pending TNF assay.

TNF Biological Assay

TNF biological activity was determined in RPMI medium containing 1% FCS.

50 $\mu$L/well of serial dilutions of samples containing TNF were added directly to the Primaria microtiter plates.

The experimental conditions utilised were the same as those previously described.

Data were analysed statistically using the one-tailed Student's t test.

Results

Lethality Induced by *E. coli* LPS in Mice Sensitised with D-Galactosamine

The results obtained in this experimental model are reported in Table 7. Compound ST 1238 significantly reduces TNF levels induced by *E. coli* LPS with both treatment schedules (pre-/post- and post-challenge only; p<0.008 and p<0.0001, respectively).

TAB 7

Effect of ST 1238, 18 mg/kg, i.v. administration on TNF production by injection of *E. coli* LPS in mice sensitised with D-galactosamine.
Pre- and post-challenge treatment schedule (−30 and +5 min) and post-challenge only treatment schedule (+5 and +30 min).

| Treatment | −30/+5 min schedule TNF (U/mL) | | | +5/+30 min shedule TNF (U/mL) | | |
|---|---|---|---|---|---|---|
| | Mean | S.D. | P | Mean | S.D. | P |
| LPS control* | 154.2 | 41.0 | — | | | |
| ST 626 (6 mg/kg, i.v.) | 35.0 | 10.0 | <0.01 | | | |
| LPS + D-GalN control | 13.6 | 4.7 | — | 18.1 | 1.8 | — |
| ST 1238 | 0.4 | 0.2 | 0.008 | 2.2 | 0.6 | 0.0001 |

*Experiment conducted with *Salmonella typhosa* LPS.

Lethality Induced by Enterotoxin SEB in Mice Sensitised with D-Galactosamine

The results obtained (Table 8) with this experimental model of TNF production induced by LPS from SEB enterotoxin in animals sensitised with D-galactosamine show that compound ST 1238 significantly reduces TNF production both with the pre-/post-challenge schedule (p<0.0001) and with the post-challenge only schedule (p<0.0002).

TAB 8

Effect of ST 1238, 18 mg/kg, i.v. administration on TNF production induced by LPS from SEB enterotoxin in mice sensitised with D-galactosamine.
Pre- and post-challenge (−30 and +5 min) and post-challenge only treatment schedule (+5 and +30 min).

| Treatment | −30/+5 min schedule TNF (U/mL) | | | +5/+30 min schedule TNF (U/mL) | | |
|---|---|---|---|---|---|---|
| | Mean | S.D. | P | mean | S.D. | P |
| SEB + D-GalN control | 240.9 | 49.4 | — | 240.9 | 49.4 | — |
| ST 1238 | 6.2 | 3.0 | 0.0001 | 27.0 | 3.9 | 0.0002 |

Evaluation of the Effect of ST 1238 on Serum Interleukin-1 Beta (IL-1 β), Interleukin-6 (IL-6) and Interferon-Gamma (IFN-γ) Induced by Enterotoxin SEB, in Mice Male BALB/c mice (C. River), aged approx. 6 weeks were utilised (10 animals per experimental group).

The animals, housed in cages at 22±2° C. and 50±15% relative humidity with 12 h of light (7 am–7 pm) and 12 h of darkness (7 pm–7 am), had unrestricted access to food and drinking water.

The compound tested was ST1238.

The substances utilised were LPS from SEB (*Staphylococcus aureus*), batch 144H4024 (Sigma) and D-galactosamine batch 031EE002485 (Merck).

Lethality was induced by *S. aureus* SEB in mice sensitised with D-galactosamine.

The experimental conditions were exactly the sane as those previously described.

Blood Samples

Blood samples were taken 2 h post-challenge for IL-6; 4 h post-challenge for IL-1β and 6 h post-challenge for IFN-g.

Ether-anaesthetised mice were bled by retro-orbital sinus puncture. Blood samples were incubated at room temperature for 2 h and the serum thus obtained was centrifuged for 20 min at 3000 rpm and stored at −80° C. until assayed.

Biological Tests

Biological tests were performed according to the procedures indicated in the respective assay kits utilised:

Mouse IL-1β Immunoassay (MLB00. R&D Systems)

Mouse IL-6 EIA Kit (8-6706,PerSeptive Diagnostics)

Mouse IFN-γ EIA Kit (8-6716,PerSeptive Diagnostics).

Data were analysed statistically using the one-tailed Student's t test.

Results

Compound ST 1238 significantly reduces the production of the inflammatory cytokines assayed (p<0.001 for IL-1β; 0.0001 for IL-6; 0.01 for IFN-γ); the results obtained are reported in Table 9.

TAB 9

Effect of ST 1238, 19 mg/kg, i.v. administration on serum levels of IL-1β, IL-6 and IFN-γ in model of intoxication with LPS from *S. aureus* SEB in mice sensitised with D-galactosamine
Pre- and post-challenge treatment schedule (−30 and +5 min).

| Treatment | IL-1β (pg/mL) | | | IL-6 (pg/mL) | | | IFN-γ (pg/mL) | | |
|---|---|---|---|---|---|---|---|---|---|
| | Mean | s.e. | P | Mean | s.e. | P | Mean | s.e. | P |
| SEB + D-galactosamine control | 18 | 4 | — | 3493 | 558 | — | 40 | 3 | — |
| ST 1238 | 0.9 | 0.5 | 0.001 | 599 | 163 | 0.0001 | 25 | 4 | 0.01 |

What is claimed is:

1. A method of treating an inflammatory and/or autoimmune pathology induced by inflammatory cytokines, which method comprises administering to a patent in need of same an effective amount of 2-aminotetraline of the formula (I)

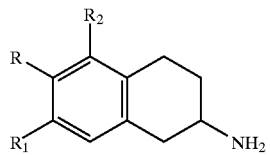

(I)

or a pharmacologically acceptable salt of the formula (II)

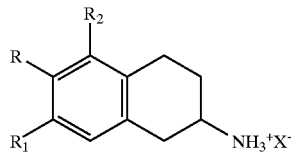

(II)

wherein:

R and $R_1$ are independently halogen, hydroxy, or $C_1$–$C_4$ alkoxy optionally substituted in position ω with a group selected from OH, $NH_2$ or $NR_3R_4$, wherein $R_3$ and $R_4$ are independently H, $C_1$–$C_4$ alkyl, unsubstituted or substituted in position ω with groups OH, $NH_2$, $C_1$–$C_4$ alkanoyl, $C_1$–$C_4$ alkyl, carbamoyl, carbamoyloxy, amino, or amino-substituted $NR_3R_4$, where $R_3$ and $R_4$ have the above meanings, $R_2$ is hydrogen, halogen, hydroxy or methoxy, with the proviso that the 2-aminotetraline excludes (a) R=$R_1$=$CH_3O$ or OH, $R_2$=H, (b) R=F, $R_1$=$CH_3O$ or OH, $R_2$=H, (c) $R_1$=$OCH_3$, R=$CH_3$ and $R_2$=H, or (d) R=$R_1$=$R_2$=$CH_3O$, and $X^-$ is the monovalent anion of a pharmacologically acceptable acid.

2. A method of preventing or treating septic shock comprising administering to a patient in need of same an effective amount of a 2-aminotetraline of the formula (I)

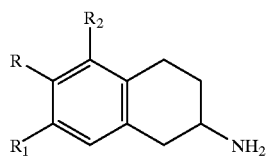

(I)

or a pharmacologically acceptable salt of the formula (II)

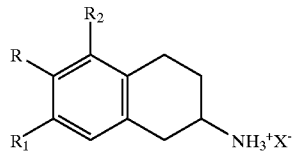

(II)

wherein:

R and $R_1$ are independently halogen, hydroxy, or $C_1$–$C_4$ alkoxy optionally substituted in position ω with a group selected from OH, $NH_2$ or $NR_3R_4$, wherein $R_3$ and $R_4$ are independently H, $C_1$–$C_4$ alkyl, unsubstituted or substituted in position ω with groups OH, $NH_2$, $C_1$–$C_4$ alkanoyl, $C_1$–$C_4$ alkyl, carbamoyl, carbamoyloxy, amino, or amino-substituted $NR_3R_4$, where $R_3$ and $R_4$ have the above meanings, $R_2$ is hydrogen, halogen, hydroxy or methoxy, with the proviso that the 2-aminotetraline excludes (a) R=$R_1$=$CH_3O$ or OH, $R_2$=H, (b) R=F, $R_1$=$CH_3O$ or OH, $R_2$=H, (c) $R_1$=$OCH_3$, R=$CH_3$ and $R_2$=H, or (d) R=$R_1$=$R_2$=$CH_3O$, and $X^-$ is the monovalent anion of a pharmacologically acceptable acid.

3. A method of treating an inflammatory and/or autoimmune pathology induced by inflammatory cytokines, which method comprises administering to a patent in need of same an effective amount of a compound selected from the group consisting of:

S(−)-2-amino-6-fluoro-7-hydroxytetraline hydrochloride;
R(+)-2-amino-6-fluoro-7-hydroxytetraline hydrochloride;
(R,S)-2-amino-5,6-difluoro-7-methoxytetraline hydrochloride;
(R,S)-2-amino-6-fluoro-7-methyltetraline hydrochloride;
(R,S)-2-amino-7-fluoro-6-hydroxytetraline hydrochloride;
(R,S)-7-acetyl-2-amino-6-methyltetraline hydrochloride; and
(R,S)-2-amino-7-fluoro-6-methoxytetraline hydrochloride.

4. A method of preventing or treating septic shock comprising administering to a patient in need of same an effective amount of a compound selected from the group consisting of:

S(−)-2-amino-6-fluoro-7-hydroxytetraline hydrochloride;
R(+)-2-amino-6-fluoro-7-hydroxytetraline hydrochloride;
(R,S)-2-amino-5,6-difluoro-7-methoxytetraline hydrochloride;
(R,S)-2-amino-6-fluoro-7-methyltetraline hydrochloride;
(R,S)-2-amino-7-fluoro-6-hydroxytetraline hydrochloride;
(R,S)-7-acetyl-2-amino-6-methyltetraline hydrochloride; and
(R,S)-2-amino-7-fluoro-6-methoxytetraline hydrochloride.

* * * * *